United States Patent
Chrisman

(10) Patent No.: US 10,478,599 B2
(45) Date of Patent: Nov. 19, 2019

(54) COMPRESSION TORQUE DEVICE

(71) Applicant: Vascugenix LLC, Little Rock, AR (US)

(72) Inventor: Freddy Dwight Chrisman, Little Rock, AR (US)

(73) Assignee: Vascugenix LLC, Little Rock, AR (US)

( * ) Notice: Subject to any disclaimer, the term of this patent is extended or adjusted under 35 U.S.C. 154(b) by 224 days.

(21) Appl. No.: 15/354,656

(22) Filed: Nov. 17, 2016

(65) Prior Publication Data
US 2018/0133440 A1    May 17, 2018

(51) Int. Cl.
*A61M 25/09* (2006.01)

(52) U.S. Cl.
CPC ........... *A61M 25/09041* (2013.01); *A61M 2025/09116* (2013.01); *A61M 2025/09125* (2013.01)

(58) Field of Classification Search
CPC .............................. A61M 25/09041
USPC ....................................... 600/585
See application file for complete search history.

(56) References Cited

U.S. PATENT DOCUMENTS

| | | |
|---|---|---|
| 3,312,128 A | 4/1967 | Wasson |
| D329,698 S | 9/1992 | Loney et al. |
| 5,161,534 A | 11/1992 | Berthiaume |
| 5,312,338 A | 5/1994 | Nelson |
| 5,325,868 A | 7/1994 | Kimmelstiel |
| 6,030,349 A | 2/2000 | Wilson et al. |
| 6,533,772 B1* | 3/2003 | Sherts ............... A61M 25/0113 279/42 |
| 6,714,809 B2 | 3/2004 | Lee |
| 7,455,660 B2 | 11/2008 | Schweikert |
| 7,717,865 B2 | 5/2010 | Boutillette |
| 7,972,282 B2 | 7/2011 | Clark et al. |
| 8,025,629 B2 | 9/2011 | Shelton |
| 8,147,481 B2 | 4/2012 | Whittaker et al. |

(Continued)

FOREIGN PATENT DOCUMENTS

| | | |
|---|---|---|
| EM | 004003358-0001 | 5/2017 |
| EM | 004003358-0002 | 5/2017 |
| EM | 004003358-0003 | 5/2017 |

OTHER PUBLICATIONS

Product Description, "H₂OTORQ", Merit Medical, 2 pages, found at http://cloud.merit.com/catalog/Brochures/400716001-C.pdf, accessed in 2014.

(Continued)

*Primary Examiner* — Daniel L Cerioni
(74) *Attorney, Agent, or Firm* — Evan Law Group LLC

(57) ABSTRACT

A compression torque device comprises a housing, an actuator, a flexible clamping member and a linear lumen. The housing comprises a body, a handle, a leading portion and an actuator opening. The actuator is operably coupled to the housing at the actuator opening. The linear lumen passes through the housing and is contiguous with the actuator opening. The actuator pivots between a first position and a second position, such that the flexible clamping member extends into the lumen when the actuator is in the first position and does not extend into the lumen when the actuator is in the second position. The actuator and the flexible clamping member may be monolithic. A kit for catheter-based intervention comprises a compression torque device and an adaptor.

13 Claims, 7 Drawing Sheets

(56) References Cited

U.S. PATENT DOCUMENTS

| | | | |
|---|---|---|---|
| 8,700,130 B2 | 4/2014 | Iddan | |
| 8,840,568 B2 | 9/2014 | Kimura | |
| 8,926,529 B2 | 1/2015 | Rollins | |
| 9,011,351 B2 | 4/2015 | Hoshinouchi | |
| 9,050,438 B2 | 6/2015 | Rollins | |
| 9,295,815 B2 | 3/2016 | Stevens et al. | |
| 9,375,553 B2 | 6/2016 | Chrisman | |
| 9,615,951 B2 | 4/2017 | Bennett et al. | |
| D810,933 S | 2/2018 | Chrisman | |
| 2005/0245847 A1* | 11/2005 | Schaeffer | A61M 25/09041 600/585 |
| 2007/0219467 A1 | 9/2007 | Clark et al. | |
| 2009/0124934 A1 | 5/2009 | Rabbitte et al. | |
| 2010/0305475 A1* | 12/2010 | Hinchliffe | A61M 25/09 600/585 |
| 2014/0296706 A1* | 10/2014 | Chronos | A61F 2/2496 600/424 |
| 2014/0324026 A1 | 10/2014 | Chrisman | |
| 2015/0157829 A1* | 6/2015 | Bunch | A61M 25/02 604/174 |
| 2016/0121086 A1* | 5/2016 | Castro | A61M 25/09041 600/585 |
| 2016/0228682 A1* | 8/2016 | Graham | A61M 25/0097 |
| 2016/0256667 A1* | 9/2016 | Ribelin | A61M 25/0618 |

OTHER PUBLICATIONS

Product Description, "Alligatork", Perouse Medical, 2 pages, found at http://perousemedical.com/wp-content/uploads/2016/02/Alligatork_december_2014_GB_HD.pdf, (2014).
R1, 9 Pages, Oct. 18, 2017, U.S. Appl. No. 29/584,792, US.
R2, 4 Pages, Nov. 10, 2017, 201730179403.1, CN.

* cited by examiner

COMPRESSION TORQUE DEVICE

BACKGROUND

A catheter-based intervention involves the insertion of a catheter into the vascular system for diagnostic or therapeutic treatment. The intervention often involves the insertion of a guidewire through a blood vessel. The guidewire is inserted and manipulated with the aid of a torque device that is removably attached to the guidewire.

Maintaining accurate control and placement of a guidewire during a medical interventional procedure is essential. Present torque devices used to accomplish this task require excessive manipulation with more than one hand or excessive force parallel to the guide wire axis in order to correctly position the device. This can divert the attention of the interventionalist during the procedure and increase the chance of unwanted movement of the wire in the patient, which could lead to complications.

Most current torque devices require the interventionalist to release the guidewire to reposition the device. These moments of release of the guidewire could result in unexpected advancement or retraction of the guidewire that could lead to problems during the procedure. The guidewire may even be pulled out of the treatment vessel altogether. Movement of the guidewire may result in longer procedures for the patient and the interventionalist, and may cause serious internal harm such as damage to the treatment vessel or abrupt vessel closure.

Existing devices require an interventionalist to perform the following steps to introduce a guidewire to a catheter: (1) insert an introducer through an adaptor coupled to the catheter, such as a Tuohy-Borst adaptor; (2) insert the guidewire through the introducer and into the catheter; (3) remove the introducer from the adaptor while leaving the guidewire in place; and (4) attach a compression torque device to the guidewire for manipulating the guidewire through the catheter. This process requires the interventionalist to release and reposition the various components during the procedure, which increases the possibility of unwanted movement of the introducer, adaptor and guidewire.

An improved compression torque device that may be operated using only one-handed blind operation is described in U.S. Pat. No. 9,375,553 to Freddy Dwight Chrisman (the "'553 patent"). The compression torque device includes a housing having a first opening that accommodates a guidewire and a second opening; an actuator that passes through the second opening which is actuated by a finger in a direction substantially perpendicular to an axis of the guidewire; a clamp operably coupled to the actuator that compresses the guidewire to couple the guidewire to the housing when pressure is applied to the actuator; and a return spring that supplies pressure to remove the clamp from the guidewire. The compression torque device allows an interventionalist to reposition and manipulate the guidewire and the torque device with a single hand, without diverting attention away from the procedure image or the patient.

SUMMARY

In a first aspect, the invention is a compression torque device comprising a housing, an actuator, a flexible clamping member and a linear lumen. The housing comprises a body, a handle, a leading portion and an actuator opening, in the body. The actuator is operably coupled to the housing at the actuator opening. The linear lumen passes through the housing and is contiguous with the actuator opening. The actuator and the flexible clamping member are monolithic. The actuator pivots between a first position and a second position, such that the flexible clamping member extends into the lumen when the actuator is in the first position and does not extend into the lumen when the actuator is in the second position.

In a second aspect, the invention is a compression torque device comprising a housing, an actuator, a linear lumen and an introducer. The actuator is operably coupled to the housing for physically engaging a guidewire. The linear lumen passes through the housing. The introducer is coupled to the housing.

In a third aspect, the invention is a compression torque device comprising a housing, an actuator, a clamping member and a linear lumen. The housing comprises a body, a handle, a leading portion and an actuator opening, in the body. The actuator is operably coupled to the housing at the actuator opening. The linear lumen passes through the housing and is contiguous with the actuator opening. The actuator and the clamping member are monolithic. The actuator pivots between a first position and a second position, such that the clamping member extends into the lumen when the actuator is in the first position and does not extend into the lumen when the actuator is in the second position. The compression torque device does not include a spring.

Definitions

The term "catheter-based intervention" means a medical procedure that involves the insertion of a catheter into a patient's body. The medical procedure may be diagnostic, such as angiography, or therapeutic, such as the insertion of a stent.

The term "interventionalist" means a medical professional that performs a catheter-based intervention.

A "Tuohy-Borst adaptor" is a medical device that attaches to a catheter to provide hemostasis while allowing other medical devices to be inserted into the catheter.

The term "hemostasis" means preventing blood loss from the body.

The term "introducer" means a member for introducing a guidewire into a catheter, often by passing through an adaptor coupled to the end of the catheter that remains outside a patient's body during a catheter-based intervention.

BRIEF DESCRIPTION OF THE DRAWINGS

The invention can be better understood with reference to the following drawings and description.

DETAILED DESCRIPTION

Although the compression torque device described in the '553 patent is a significant improvement over existing torque devices, it could be further improved by reducing the total number of components in the device. Reducing the number of device components would reduce the cost and complexity of manufacture, and may allow manufacturers to produce the device using previously unavailable manufacturing techniques. For example, eliminating a metal spring would result in a compression torque device that could be produced entirely by injection molding.

The present invention is a compression torque device that includes a minimal number of components. This device provides all of the advantages of the compression torque device described in the '553 patent, such as one-handed blind operation, but achieves these advantages with significantly fewer components. The compression torque device includes a housing, an actuator operably coupled to the housing, a clamping member and a lumen, passing through the housing. The actuator and the clamping member may be monolithic, which allows the compression torque device to be composed of as little as two pieces. Reducing the number of components in the compression torque device provides many manufacturing advantages. The inclusion of fewer total parts greatly simplifies the manufacturing process. The device may be manufactured in fewer steps, which saves time and facilitates automated manufacturing. Having fewer parts reduces the number of points in the manufacturing process where manufacturing errors may occur and reduces the number of components that are subject to failure in the finished device. The compression torque device may be free of metal components, which enables the use of manufacturing processes that would not be possible with a more complex device, such as injection molding. These manufacturing advantages will reduce the manufacturing costs.

Figure 1:
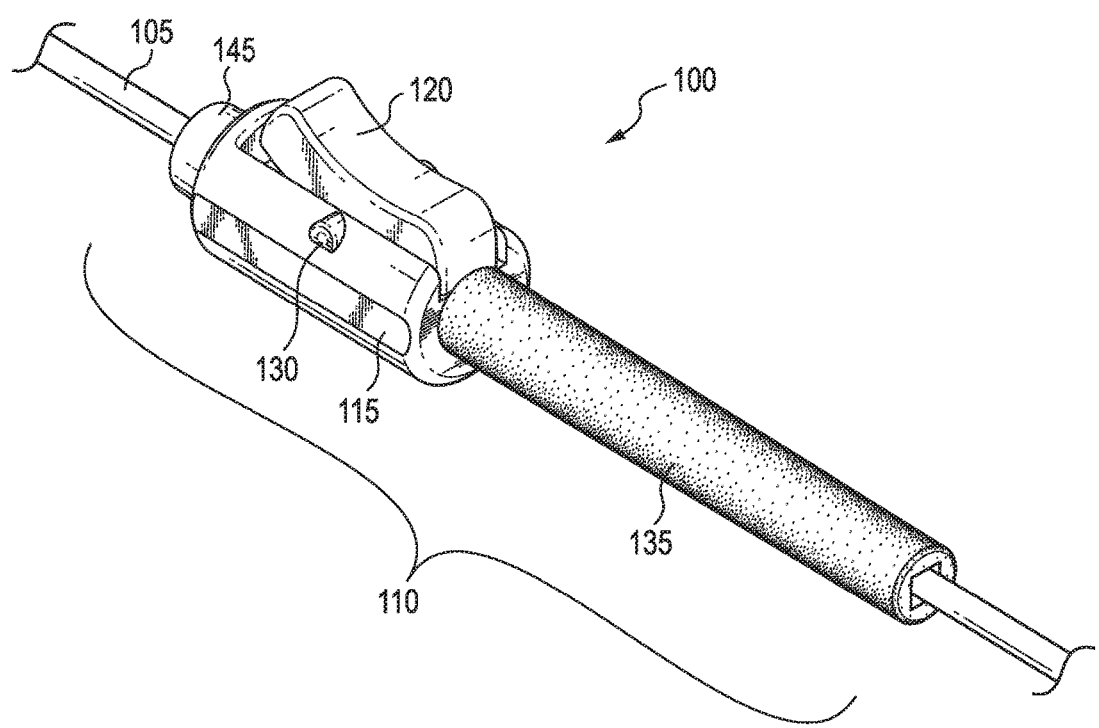
FIG. 1 illustrates a compression torque device and a guidewire.

FIG. 1 illustrates a compression torque device 100 and a guidewire 105. The compression torque device includes a housing 110 and an actuator 120. The housing includes a body 115, a handle 135 and a leading portion 145. The housing may be monolithic. The leading portion may optionally include a fitting (not shown) to allow components to be removably coupled to the housing. For example, the leading portion may include a Luer fitting, such as a Luer slip fit fitting or a Luer lock fitting (see FIG. 7A). The actuator is operably coupled to the body, such as by a snap fit or press fit, at a hinge point 130 and may pivot about the hinge point. Preferably, the housing and the actuator are designed to eliminate the need for a separate hinge component. For example, the actuator may have a first shaft that passes through a first opening at the hinge point, and a second shaft, opposite the first shaft, that passes through a second opening, opposite the first opening, at the hinge point. Eliminating a separate hinge minimizes the total number of components in the compression torque device and also allows for the device to be free of metal, which in turn simplifies manufacturing. Although the hinge point is visible on the exterior of the housing in FIG. 1, the housing and actuator could alternatively be designed so that the hinge point is located in the interior of the housing.

Figure 2A:
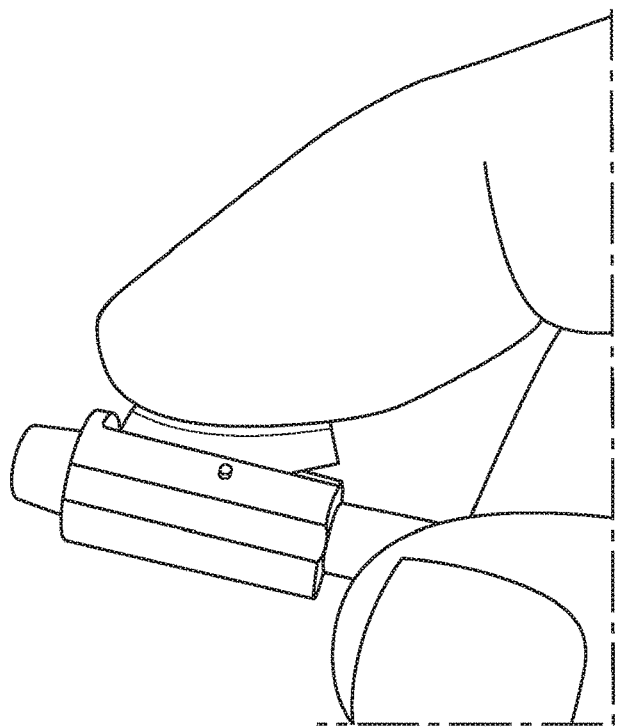
FIG. 2A is a photograph of a compression torque device in a first position, for physically engaging a guidewire.
Figure 2B:
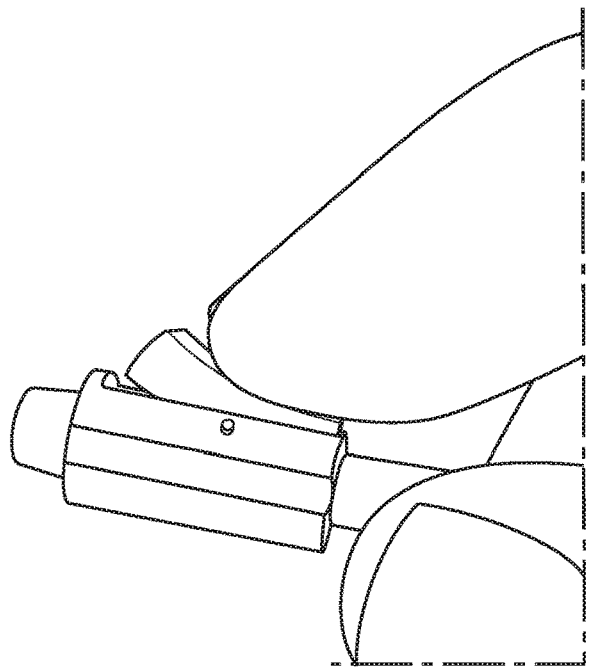
FIG. 2B is a photograph of a compression torque device in a second position, for not physically engaging a guidewire.

FIG. 2A is a photograph of a compression torque device in a first position, for physically engaging a guidewire (not shown). FIG. 2B is a photograph of a compression torque device in a second position, for not physically engaging a guidewire (not shown). The actuator may be toggled between the first position and the second position by pivoting about the hinge. In the first position, the actuator physically engages the guidewire to couple the compression torque device to the guidewire such that movement of the compression torque device results in movement of the guidewire, which allows an interventionalist to torque, reposition, or otherwise manipulate the guidewire. In the second position, the actuator is not physically engaged to the guidewire and the compression torque device may be moved longitudinally along the guidewire and radially around the guidewire such that movement of the compression torque device does not affect the guidewire. In the first (coupled) position, the actuator applies a downward force that is perpendicular to the guidewire. This design is safer than compression torque devices that apply a force parallel to the guidewire, since the application of a parallel force could lead to unexpected advancement or retraction of the guidewire.

Figure 7A:
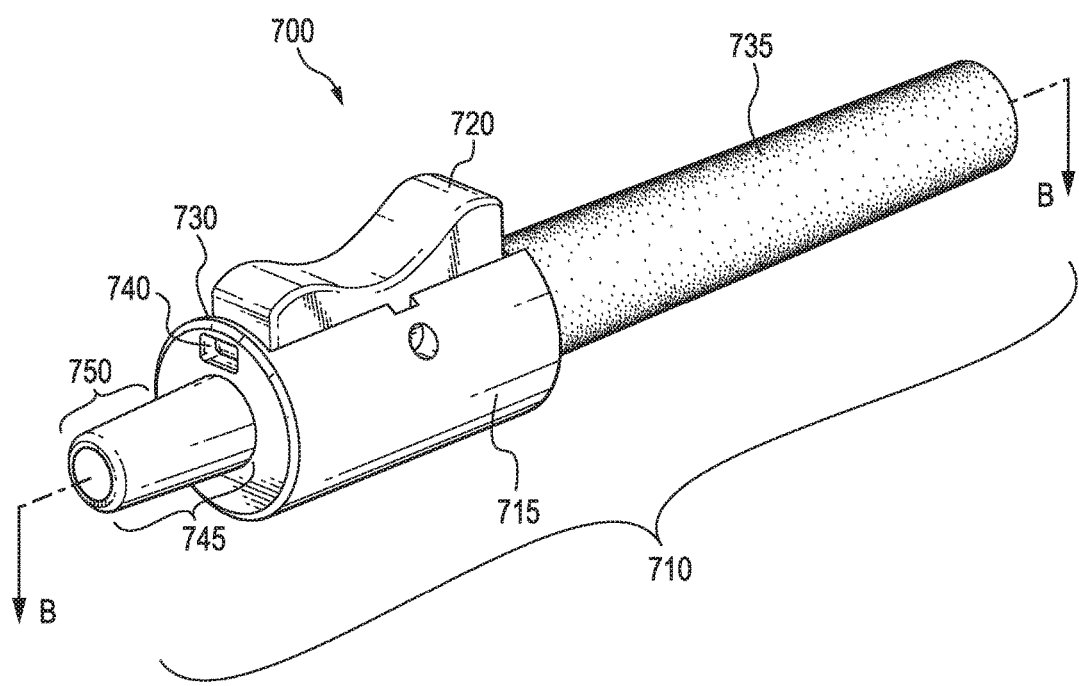
FIG. 7A illustrates an alternative configuration of a compression torque device.

FIG. 7A illustrates an alternative configuration of a compression torque device. The compression torque device 700 includes a housing 710 and an actuator 720. The actuator is shown in a first position, for physically engaging a guidewire (not shown). The housing includes a body 715, a handle 735 and a leading portion 745. The leading portion includes a Luer fitting 750. The housing includes a latch 730 for securing the actuator in the first position. The actuator includes a tab 740 that extends under the latch. The latch and the tab are sufficiently resilient and durable to allow the actuator to be repeatedly toggled between the first position and the second position without the latch or the tab breaking. The optional latch and tab prevent the unintentional movement of the actuator after the actuator has been purposefully placed in the first position. The optional latch and tab also allow an interventionalist to safely remove her hand from the compression torque device after it has been coupled to a guidewire during a catheter-based intervention without the compression torque device becoming unintentionally uncoupled from the guidewire.

Figure 3A:
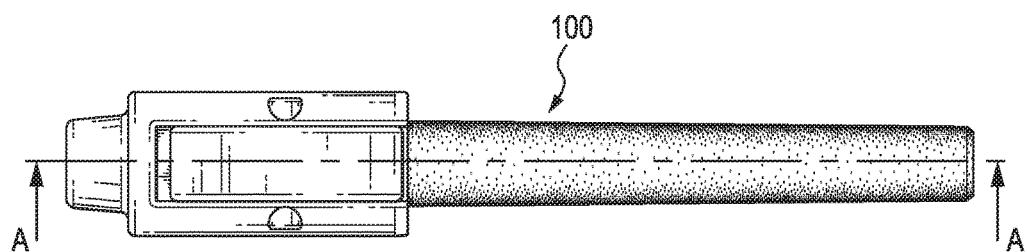
FIG. 3A illustrates a top view of a compression torque device.
Figure 3B:
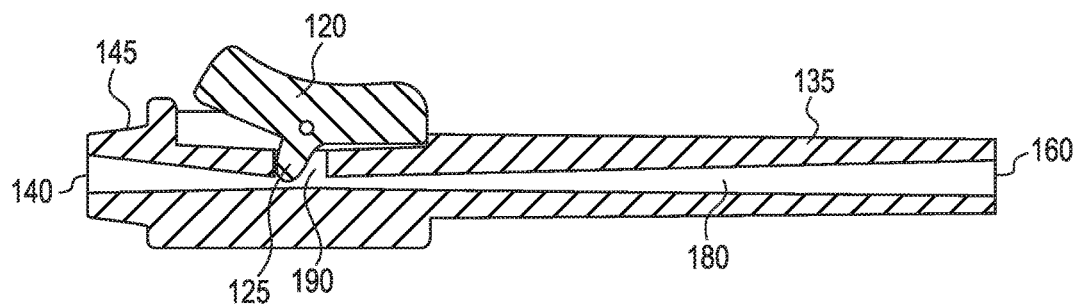
FIG. 3B illustrates a sectioned view of a compression torque device.

FIG. 3A illustrates a top view of the compression torque device 100. FIG. 3B illustrates a sectioned view of the compression torque device 100 along line AA shown in FIG. 3A. The compression torque device has a first opening 140 on the leading portion 145 of the housing and a second opening 160 on the handle 135 of the housing. The compression torque device has a linear lumen 180 passing through the center of the device between the first opening and the second opening to allow a guidewire (not shown) to pass through the device. The lumen may optionally be tapered. An actuator opening 190 in the housing is contiguous with the linear lumen. A clamping member 125 extends through the actuator opening 190. The clamping member may be rigid or may be flexible. The actuator 120 and the clamping member may be monolithic.

Figure 7B:
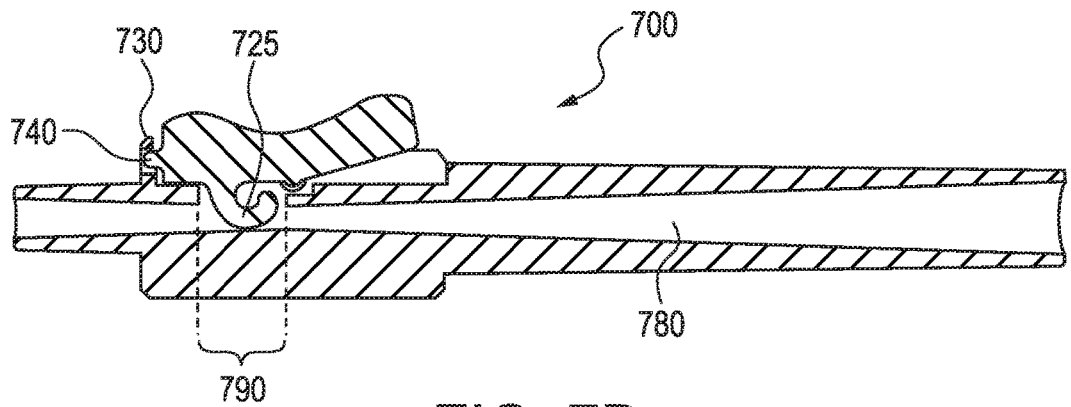
FIG. 7B illustrates a sectioned view of a compression torque device in a first position, for physically engaging a guidewire.
Figure 7C:
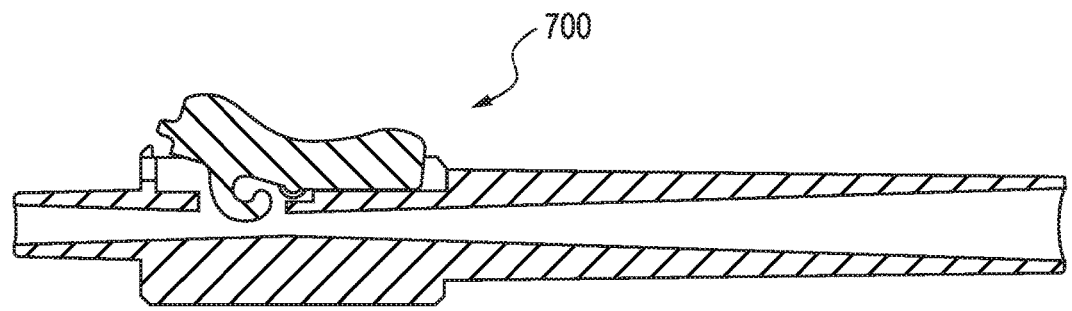
FIG. 7C illustrates a sectioned view of a compression torque device in a second position, for not physically engaging a guidewire.

FIG. 7B illustrates a sectioned view of the compression torque device 700 in a first position, for physically engaging a guidewire (not shown), along line BB shown in FIG. 7A. A flexible clamping member 725 extends through an actuator opening 790 in the housing. The flexible clamping member and the actuator may be monolithic. A linear lumen 780 passes through the housing and is contiguous with the actuator opening. As may be seen in FIG. 7B, the flexible clamping member extends into the linear lumen when the actuator is in a first position, for physically engaging a guidewire (not shown). FIG. 7C illustrates a sectioned view of the compression torque device 700 in a second position, for not physically engaging a guidewire (not shown), along line BB shown in FIG. 7A. As may be seen in FIG. 7C, the flexible clamping member does not extend into the linear lumen when the actuator is in the second position.

The actuator and the clamping member may have a variety of configurations while still being capable of physically engaging a guidewire when the actuator is in a first position and not physically engaging the guidewire when the actuator is in a second position. For example, the hinge point may be located at any suitable location along the actuator that allows the actuator to be physically coupled to the housing and pivot between the first position and the second position. Similarly, the clamping member may be located at any position along the actuator that allows the clamping member to pass through the actuator opening. The shape of the clamping member may be varied to achieve a desired coupling of the compression torque device with the guidewire. For example, FIG. 3B illustrates a clamping member that is a protrusion that extends from the actuator while FIGS. 7B and 7C illustrate a flexible clamping member that acts as a spring with a clamping surface. The flexible clamping member acts as a spring and resiliently compresses the guidewire when physically engaging a guidewire. The clamping member may have any configuration that allows it to physically engage a guidewire, such as having a spherical tip, a hemispherical tip, a helical coil or having a more complex spring shape than that shown in FIGS. 7B and 7C. Preferably, the actuator and the clamping member are monolithic.

The compression torque device couples to a guidewire with a minimal number of components. The compression torque device may be composed of as little as two components: a monolithic housing and a monolithic actuator including a clamping member. A monolithic housing includes a body, a handle and a leading portion as a single component, while also including an actuator opening and a lumen passing through the housing and contiguous with the actuator opening. The actuator may be toggled by hand and does not require any additional components to transition between coupled and uncoupled positions. This design reduces the total number of components in the compression torque device and may be constructed without any components composed of metal, simplifying manufacturing.

The compression torque device is suitable for use with all types of guidewires, including, for example, stainless steel core guidewires, nitinol core guidewires, tapered core guidewires, parabolic core guidewires, guidewires with shaping ribbon tips, guidewires with coil covers, guidewires with tapered coil covers, guidewires with polymer covers, guidewires with exposed coils, guidewires with hydrophobic coatings, guidewires with hydrophilic coatings, workhorse guidewires, guidewires with extra support or specialty guidewires. The compression torque device is capable of accommodating guidewires having a variety of diameters. The first opening, the second opening and the lumen may have a diameter of 0.001 to 0.20 inches, preferably 0.01 to 0.1 inches, including 0.01 inches, 0.02 inches, 0.03 inches, 0.04 inches, 0.05 inches, 0.06 inches, 0.07 inches, 0.08 inches and 0.09 inches. The compression torque device may be color coded to indicate the guidewire diameter range that it may accommodate. For example, a compression torque device designed to be used with guidewires having a diameter of 0.025-0.040 inches may be colored orange, while a compression torque device designed to be used with guidewires having a diameter of 0.010-0.020 inches may be colored blue.

Figure 4A:
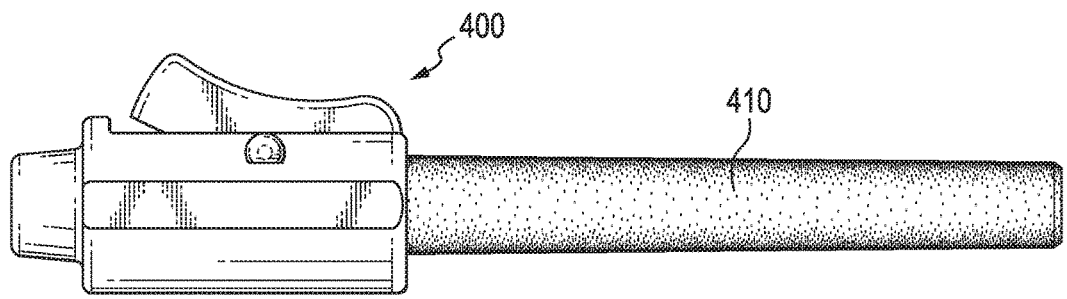
FIG. 4A illustrates a compression torque device with a textured handle.
Figure 4B:
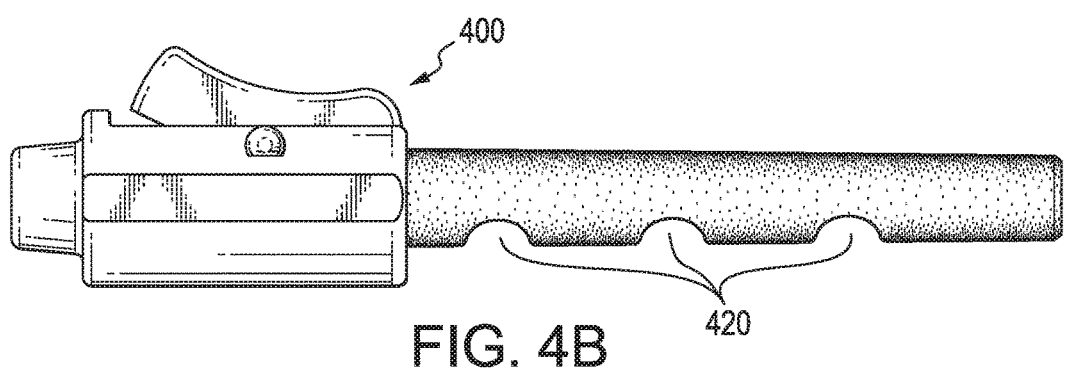
FIG. 4B illustrates a compression torque device with one or more finger grips.
Figure 4C:
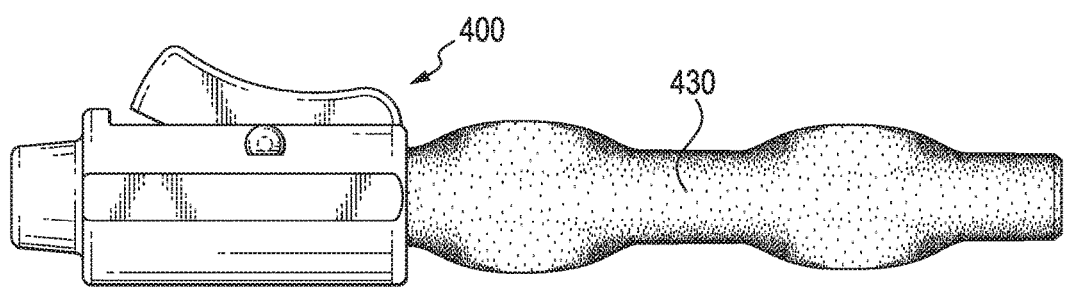
FIG. 4C illustrates a compression torque device with a contoured handle.

The compression torque device may optionally include design features that will facilitate its manipulation by the interventionalist. FIG. 4A illustrates a compression torque device 400 with a textured handle 410. The housing may be textured to provide enhanced grip to the interventionalist. For example, the housing may include textures such as bumps, dots, ridges, lines or depressions. FIG. 7A illustrates a handle with a diamond pattern. Alternatively, a textured coating may be applied to a smooth housing to produce a compression torque device with a textured housing. The texturing may cover the entire outer surface of the housing, or may only cover a portion of the outer surface of the housing. The texturing may be uniform, or may vary along the housing. FIG. 4B illustrates a compression torque device 400 with one or more finger grips 420. The finger grips may be present on one side of the compression torque device, or may be located on multiple sides of the compression torque device. FIG. 4C illustrates a compression torque device 400 with a contoured handle 430. The shape of the handle may be designed to provide an ergonomic grip for the interventionalist.

The compression torque device may be composed of any rigid, durable material. Suitable materials include plastics, metals and composites. Preferably, the compression torque device is composed of plastic. Preferred plastics include acrylonitrile butadiene styrene (ABS), acrylonitrile butadiene styrene/polycarbonate (ABS/PC), engineered thermoplastic polyurethane (ETPU), high density polyethylene (HDPE), liquid crystal polymer (LCP), low density polyethylene (LDPE), linear low density polyethylene (LLDPE), polyamide (PA or nylon), polybutylene terephthalate (PBT), polycarbonate (PC), polycarbonate/polybutylene terephthalate (PC/PBT), polyetheretherketone (PEEK), polyether imide (PEI, such as ULTEM®), polyethylene terephthalate (PET), copolyester, poly(methyl methacrylate) (PMMA), polyoxymethylene (POM), polypropylene (PP), polyphenylene ether/polystyrene (PPE/PS), polyphenylene sulfide (PPS), polystyrene (PS), polysulfone (PSU), styrene butadiene (SB), thermoplastic elastomer/thermoplastic vulcanizate (TPE/TPV), thermoplastic polyurethane elastomer (TPU), and mixtures thereof.

The compression torque device may be produced by any suitable manufacturing process, such as injection molding, extrusion, or additive manufacturing (3D printing). Preferably, the compression torque device is produced by injection molding. The housing and the actuator may be produced as two separate pieces that are assembled to form the final product. Alternatively, the housing and the actuator may be produced as a single component with a thin piece of material connecting the two pieces that is easily broken with the initial movement of the actuator.

Figure 5:
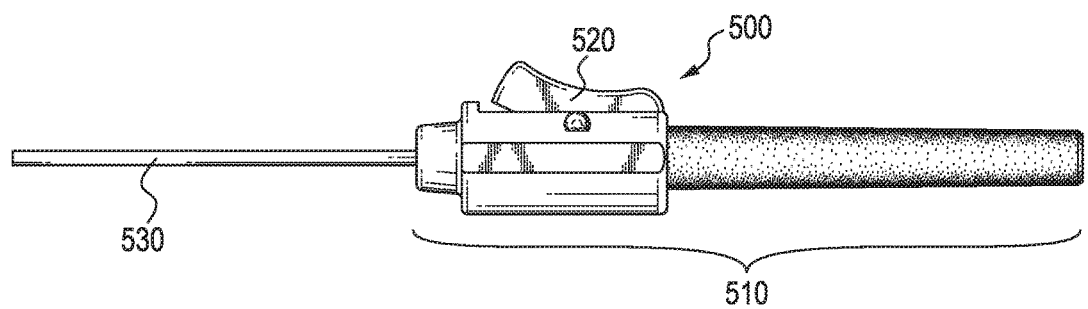
FIG. 5 illustrates a compression torque device that includes a housing, an actuator and an optional introducer.

FIG. 5 illustrates a compression torque device 500 that includes a housing 510, an actuator 520, operably coupled to the housing, and an optional introducer 530, coupled to the housing. The introducer is a member for introducing a guidewire into a catheter, often by passing through a Tuohy-Borst adaptor coupled to the end of the catheter that remains outside a patient's body during a catheter-based intervention. The introducer may be removably coupled to the housing, for example, by a press fit, an adhesive, or threading. Alternatively, the introducer and the housing may be monolithic. The introducer may be composed of any rigid, durable material. Suitable materials include plastics, metals and composites. Preferably, the introducer is composed of plastic, and suitable plastics include the preferred plastics for injection molding described above. The plastic used in the introducer may be the same type of plastic used in the compression torque device, or may be a different plastic. The introducer may optionally be radiopaque for detection by X-rays or other suitable imaging techniques.

A compression torque device that includes an introducer offers a number of advantages to an interventionalist. Current commercially-available introducers and compression torque devices are not designed to be physically coupled. Existing devices require an interventionalist to perform the following steps to introduce a guidewire to a catheter: (1) insert an introducer through an adaptor coupled to the catheter, such as a Tuohy-Borst adaptor; (2) insert the guidewire through the introducer and into the catheter; (3) remove the introducer from the adaptor while leaving the guidewire in place; and (4) attach a compression torque device to the guidewire for manipulating the guidewire through the catheter. By contrast, a compression torque device that includes an integral introducer, or that may be coupled to an introducer, allows an interventionalist to introduce a guidewire to a catheter by performing the following steps: (1) if necessary, couple the introducer to the compression torque device; (2) insert the introducer of the compression torque device through an adaptor coupled to the catheter; and (3) insert the guidewire through the compression torque device and the introducer into the catheter. Eliminating the need to remove the introducer and replace it with a separate compression torque device will save time during the intervention, reducing the duration of the procedure for the patient potentially allowing the interventionalist to complete more interventions in a given time frame. It will also eliminate the possibility that the guidewire becomes inadvertently repositioned during the process of removing the introducer and replacing it with the compression torque device.

Figure 6:
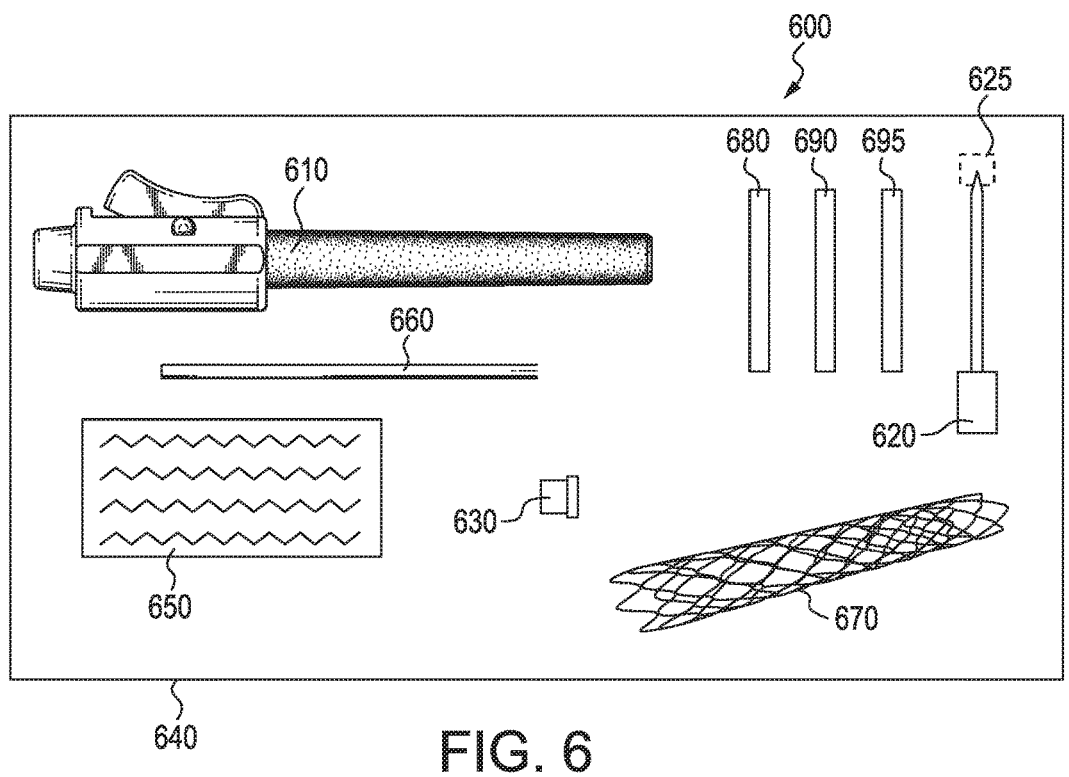
FIG. 6 illustrates a kit for catheter-based intervention.

FIG. 6 illustrates a kit 600 for catheter-based interventions. The kit includes a compression torque device 610 and an adaptor 630. The kit may optionally be housed in a container 640. Optional printed instructions 650 describe how to use the compression torque device. The kit may optionally include an introducer needle 620, which may include an optional cap 625 to protect the sharp end of the needle. Alternatively, the kit may optionally include an introducer 660 that may be coupled to the compression torque device, or may include a compression torque device with a housing and introducer that are monolithic. The kit may optionally include a therapeutic intervention device 670, such as a stent as shown. The kit may optionally include additional components used in catheter-based interventions, such as a catheter 680, a guidewire 690 and/or a pusher 695. Preferably, the compression torque device, the adaptor and any optional kit components are sterile.

The introducer needle is a member for passing a guidewire through the adaptor and into a catheter. The introducer needle may be composed of any rigid, durable material. Suitable materials include plastics, metals and composites. The introducer needle may optionally include a cap.

The adaptor couples to the portion of the catheter that remains outside of a patient's body during the catheter-based intervention to provide hemostasis. Suitable adaptors include, for example, Tuohy-Borst adaptors and hemostatic Y-connectors.

The kit may optionally include instructions for use. The instructions may be provided as printed instructions or in electronic format, such as on a universal serial bus (USB) drive, on a secure digital (SD) card, or hosted over the internet and accessible through a quick response (QR) code.

The kit may optionally include a container for housing the kit ingredients. Preferably, the contents of the kit are sterile and ready for use. The container protects the compression torque device, guidewire and any other components from damage and contamination. The container may be formed of a rigid, durable material, such as plastic, or may be flexible, such as a bag or soft-sided box.

The kit may optionally include a therapeutic intervention device. The therapeutic intervention device is a device that may be inserted into a vein or artery to provide a therapeutic benefit to a patient in need thereof. The therapeutic intervention device may be placed by passing it along the length of a guidewire that has been inserted through a catheter to a desired treatment location. Examples of therapeutic intervention devices include stents, coronary stents, vascular stents, drug-eluting stents and balloons.

The kit may optionally include components used in catheter-based interventions. Examples of components used in catheter-based interventions include guidewires, catheters, and pushers. The inclusion of these components may allow a single kit to provide all the necessary equipment for completing a catheter-based intervention. A comprehensive kit may be especially useful for interventionalists practicing in less-developed areas or in settings with limited resources.

EXAMPLES

Example 1—General Interventional Protocol

A catheter-based intervention begins by placing a patient on a procedural table (also known as a catheter table) and placing a sterile drape over the patient up to his or her neck. A maneuverable X-ray imaging tube surrounds the patient and the table. A sterile equipment table is located in the same room and may be accessed by a physician and a technician. Typically, the technician assists the physician by providing equipment from the sterile equipment table, maneuvering the X-ray imaging tube and acquiring extra equipment in a sterile manner from other workers in the room as needed.

The patient's vascular system may be accessed through any artery, with the femoral artery being the most common artery used. A local anesthetic, such as lidocaine, is used to numb the skin at the access point. After the skin has been numbed, an access needle is used to puncture the skin to gain access to a blood vessel. Once there is blood flow from the access needle, a wire is introduced through the access needle and into the vessel. After inserting the wire into the vessel, the needle is removed. The wire remains in the vessel with a portion of the wire extending outside of the patient's body. The external portion of wire is used as a guide to advance an access sheath over the wire and into the vessel. After the access sheath has been inserted into the vessel, the wire is removed. The access sheath in position in the vessel provides hemostasis at the access point.

A catheter is then advanced through the access sheath and up to the vessel needing treatment. Catheters are available in a variety of lengths, sizes and shapes and the interventionalist selects the appropriate catheter for the specific intervention being performed. Proper placement of the catheter is confirmed by X-ray. A portion of the catheter remains outside of the patient's body.

A Tuohy-Borst adaptor is then placed on the end of the catheter that remains outside of the patient's body. The Tuohy-Borst adaptor is a hemostatic valve system that has two ports. One port is typically used to connect an external monitor, such as a pressure sensing device for monitoring the patients' blood pressure during the procedure. The other port is used as an access port to advance interventional devices through the catheter and into the treatment vessel.

In a first method, a guidewire is advanced through the Tuohy-Borst adaptor and into the catheter using an introducer. The introducer is inserted into the Tuohy-Borst adaptor and the guidewire is inserted through the introducer into the catheter. The introducer is then removed from the Tuohy-Borst adaptor while leaving the guidewire in place. A compression torque device is then coupled to the portion of the guidewire remaining outside of the patient's body for manipulating the guidewire through the catheter.

In an alternative method, the guidewire may be advanced through the Tuohy-Borst adaptor and into the catheter using a compression torque device with a housing and introducer that are monolithic, or a compression torque device that may be coupled to an introducer. When using such a combination device, the introducer coupled to the compression torque device is inserted through the Tuohy-Borst adaptor, and the guidewire is then inserted through the compression torque device and the introducer into the catheter. A portion of the guidewire remaining outside of the patient's body may be manipulated with the compression torque device.

The guidewire is then advanced through and out of the distal end of the catheter and into the treatment vessel by manipulating the portion of the guidewire extending out of the patient's body through the Tuohy-Borst adaptor. The treatment vessel will likely have tortuosity and plaque, which requires the guidewire to be advanced and torqued to reach a stable position beyond the diseased segment being treated. The interventionalist will hold the Tuohy-Borst adaptor with one hand to maintain its stability and will hold the compression torque device with the other hand. When the compression torque device is coupled to the guidewire, the interventionalist may advance, retract or torque the distal end of the guidewire through the treatment vessel from outside of the body.

The compression torque device will need to be coupled and uncoupled from the guidewire multiple times during the catheter-based intervention. This is accomplished by pivoting an actuator on the compression torque device between a first position, which couples the compression torque device to the guidewire, and a second position, which uncouples the compression torque device from the guidewire. The interventionalist may pivot the actuator between the first position and the second position with a single finger while keeping the opposite hand securely on the Tuohy-Borst adaptor. The compression torque device may be coupled and uncoupled from the guidewire without any visual cues.

Once the guidewire is in the desired treatment location in the treatment vessel, the compression torque device is removed. A portion of the guidewire continues to extend out of the catheter and Tuohy-Borst adaptor from the patient's body. Therapeutic intervention devices, such as stents and balloons, may then be advanced along the external portion of the guidewire to the desired treatment location. Once the therapeutic intervention device has been placed in its desired location, the other components used in the intervention may be removed and the intervention may be completed.

Example 2—Cardiac Intervention (Prophetic)

A cardiac interventionalist prepares to clear an occlusion in a vessel for the insertion of a cardiac stent in an artery. Once the catheter has been established, the cardiac interventionalist grasps a compression torque device with one hand and a guidewire with her other hand. The interventionalist advances the compression torque device over the guidewire by threading the guidewire into a first opening of the compression torque device, through a lumen, and out a second opening of the device to a desired position along the guidewire. Once the compression torque device is at the desired position along the guidewire, the interventionalist uses the thumb of her hand grasping the compression torque device to toggle an actuator to a coupled mode. This action couples the compression torque device to the guidewire. After coupling the compression torque device to the guidewire, the compression torque device can be used to advance, reposition, rotate or torque the guidewire through and out the catheter as needed. The various manipulations of the guidewire can all be achieved without having to use a second hand or release the guidewire, and without depending on visualization of the compression torque device, such as by eyesight or through an imaging device. When the interventionalist needs to reposition or remove the compression torque device, she toggles the actuator to its initial uncoupled position and disengages the compression torque device from the guidewire. The compression torque device may then be moved along the guidewire in a longitudinal or rotational position, or removed from the guidewire completely, without the use of a second hand or dependence on visual cues. This process may be repeated as many times as necessary to clear the occlusion and reach the artery. After the guidewire has traversed the catheter and any occlusions, the stent may be inserted into the artery. The stent is inserted over the guidewire and advanced through the catheter using a pusher. Once the stent is in place, the pusher and the guidewire may be removed. The catheter and the additional components used in the intervention may then be removed to complete the intervention.

REFERENCES

1. U.S. Pat. App. Pub. No. 2014/0324026.
2. U.S. Pat. No. 5,312,338.
3. U.S. Pat. No. 5,325,868.
4. U.S. Pat. No. 6,714,809.
5. U.S. Pat. No. 7,717,865.
6. U.S. Pat. No. 7,455,660.
7. U.S. Pat. No. 7,972,282.
8. U.S. Pat. No. 8,700,130.
9. U.S. Pat. No. 8,840,568.
10. U.S. Pat. No. 8,926,529.
11. U.S. Pat. No. 9,011,351.
12. U.S. Pat. No. 9,050,438.
13. U.S. Pat. No. 9,375,553.

What is claimed is:
1. A compression torque device, consisting of:
  a housing, comprising
    a body,
    a handle,
    a leading portion, and
    an actuator opening, in the body,
  a first opening on the leading portion,
  a second opening on the handle,
  an actuator, operably coupled to the housing at the actuator opening,
  a flexible clamping member,
  optionally, an introducer, coupled to the housing, and
  a linear lumen, passing through the housing and contiguous with the actuator opening, wherein the actuator and the flexible clamping member are monolithic and formed of the same material, the housing is monolithic, and the actuator pivots between a first position and a second position about a hinge point between ends of the actuator, such that the flexible clamping member extends further into the lumen when the actuator is in the first position and extends less into the lumen when the actuator is in the second position.

2. The compression torque device of claim 1, wherein the lumen is tapered.

3. The compression torque device of claim 1, wherein the housing comprises a latch and the actuator comprises a tab, wherein the tab passes under the latch when the actuator is in the first position, and the latch prevents unintentional movement of the actuator when the actuator is in the first position, wherein the leading portion of the hosing comprises a fitting.

4. The compression torque device of claim 1, wherein the compression torque device does not comprise metal.

5. The compression torque device of claim 1, produced by injection molding.

6. A kit for catheter-based intervention, comprising:

the compression torque device of claim 1, optionally, an introducer, and an adaptor.

7. The compression torque device of claim 1, wherein the housing is monolithic, the handle is textured, the leading portion of the housing comprises a Luer fitting, and the housing comprises a latch and the actuator comprises a tab, wherein the tab passes under the latch when the actuator is in the first position, and the latch prevents unintentional movement of the actuator when the actuator is in the first position.

8. The compression torque device of claim 1, wherein the introducer is removably coupled to the housing.

9. The compression torque device of claim 1, wherein the introducer and the housing are monolithic.

10. The compression torque device of claim 1, wherein the introducer is radiopaque.

11. The compression torque device of claim 1, wherein the handle is textured.

12. The compression torque device of claim 1, wherein the handle comprises finger grips.

13. The kit of claim 6, wherein the compression torque device and the adaptor are sterile.

* * * * *